United States Patent [19]
Gehring et al.

[11] Patent Number: 5,840,975
[45] Date of Patent: Nov. 24, 1998

[54] PROCESS FOR PREPARING NUCLEUS-HALOGENATED BENZOYL CHLORIDES

[75] Inventors: Reinhold Gehring, Wuppertal; Herbert Müller, Kreuzau; Georg Hardenbicker, Wipperfürth, all of Germany; Werner Bussmann, League City, Tex.

[73] Assignee: Bayer Aktiengesellschaft, Leverkusen, Germany

[21] Appl. No.: 875,363

[22] PCT Filed: Jan. 22, 1996

[86] PCT No.: PCT/EP96/00237

§ 371 Date: Jul. 24, 1997

§ 102(e) Date: Jul. 24, 1997

[87] PCT Pub. No.: WO96/23758

PCT Pub. Date: Aug. 8, 1996

[30] Foreign Application Priority Data

Feb. 3, 1995 [DE] Germany ............ 195 03 471.6

[51] Int. Cl.[6] .................................................. C07C 51/58

[52] U.S. Cl. ........................................................ 562/859

[58] Field of Search ......................................... 560/859

[56] References Cited

U.S. PATENT DOCUMENTS

| 1,557,154 | 10/1925 | George ................................... 562/859 |
| 1,880,169 | 9/1932 | Bennett et al. ........................ 562/859 |
| 4,276,231 | 6/1981 | Böckmann et al. .................... 562/859 |
| 5,599,980 | 2/1997 | Marhold et al. . |

FOREIGN PATENT DOCUMENTS

| 589920 | 12/1959 | Canada . |
| 1248953 | 5/1985 | Canada . |
| 4301247 | 7/1994 | Germany . |

*Primary Examiner*—Paul J. Killos
*Attorney, Agent, or Firm*—Sprung Kramer Schaefer & Briscoe

[57] ABSTRACT

Ring-halogenated benzoyl chlorides are obtained in a particularly advantageous manner if ring-halogenated benzotrichlorides are reacted with formic acid in the presence of iron salts.

9 Claims, No Drawings

PROCESS FOR PREPARING NUCLEUS-HALOGENATED BENZOYL CHLORIDES

The present invention relates to a particularly advantageous process for the preparation of ring-halogenated benzoyl chlorides from the corresponding benzotrichlorides.

DE-A 4 301 247 discloses that certain ring-halogenated benzoyl chlorides can be prepared by partially saponifying the corresponding ring-halogenated benzotrichlorides with water in the presence of iron(III) chloride. A disadvantage in this process is that corrosive reaction mixtures must be handled (e.g. water, hydrochloric acid, iron salts and possibly liquids containing fluoride ions). Therefore, in an industrial application of this process, reaction vessels made of special materials would frequently have to be used. In addition intense exothermic reactions frequently occur due to autocatalysis, so that particular measures are necessary for their control.

A process has now been found for the preparation of ring-halogenated benzoyl chlorides, which is characterized in that ring-halogenated benzotrichlorides are reacted with formic acid in the presence of iron salts.

In the process according to the invention, fluorinated and/or chlorinated benzotrichlorides, for example, can be used. Preferably, use is made of benzotrichlorides of the formula (I)

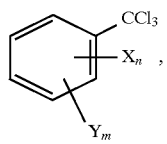

in which

X represents fluorine and Y represents hydrogen or chlorine and n denotes an integer from 1 to 5 and m=5-n.

Particularly preferred benzotrichlorides are 2,4-dichloro-5-fluoro-benzotrichloride, 2,3,5,6-tetrafluoro-benzotrichloride, 2,3,4-trifluoro-5-chloro-benzotrichloride and 2,3,4-trifluoro-benzotrichloride, in particular preference is given to 2,3,4,5-tetrafluoro-benzotrichloride. Ring-halogenated benzotrichlorides which can be used are known compounds or can be prepared analogously to the known compounds.

Formic acid can be used in the process according to the invention, e.g. in amounts of 0.8 to 1.1 mol per mole of ring-halogenated benzotrichloride. Preferably, this amount is 0.95 to 1.05 mol, particularly preferably 1 mol.

A suitable iron salt is, in particular, iron(III) chloride. Iron salts can be used, e.g. in amounts of 0.05 to 3% by weight, based on ring-halogenated benzotrichloride. Preferably, this amount is 1 to 2% by weight.

The process according to the invention can be carried out, for example at temperatures in the range 20° to 100° C. Preference is given to temperatures in the range 40° to 70° C.

The pressure at which the process according to the invention is carried out is not critical. Reduced pressure, atmospheric pressure or superatmospheric pressure may be employed. Preferably, atmospheric pressure is employed.

Suitable materials for apparatuses for carrying out the process according to the invention are, for example, stainless steels.

During the reaction according to the invention, 1 mol of carbon monoxide and 2 mol of hydrogen chloride escape from the reaction mixture per mole of formic acid reacted. The hydrogen chloride can be absorbed in water and the hydrochloric acid thus obtained can be further used for the most varied purposes. The carbon monoxide can be burnt.

The reaction according to the invention proceeds rapidly. This means that formic acid can be metered in at the same rate as it reacts. The consumption of formic acid can be followed by monitoring the carbon monoxide content in the exhaust gas.

After the process according to the invention has been carried out, a reaction mixture is generally present, such that it essentially contains the ring-halogenated benzoyl chloride prepared and a mixture containing iron salts. The ring-halogenated benzoyl chloride prepared can be separated off from the reaction mixture, e.g. by distillation. The mixture containing iron salts then remaining can be reused in a further batch instead of fresh iron salts. If the mixture containing iron salts is recycled repeatedly, it is advantageous to add a small amount of fresh iron salts, in particular iron(III) chloride, from time to time, e.g. after every second to fifth recycling, 10% to 50% by weight of the amount of iron salts originally used.

Ring-halogenated benzoyl chlorides, as are particularly readily obtainable in the manner according to the invention, are important intermediates in the preparation of antiinfective medicaments (see, for example, DE-A 3 420 770 and EP-A 417 669).

The process according to the invention has a number of advantages. It can be carried out in apparatuses made of conventional materials, since less corrosive reaction mixtures are produced in it than in known processes. Furthermore, using the process according to the invention, ring-halogenated benzoyl chlorides can be prepared in yields of generally above 90%, and it can be allowed to proceed under metering control.

EXAMPLES

Percentages are by weight, unless otherwise stated.

Example 1

2,3,5,6-Tetrafluorobenzoyl chloride 268 g of 2,3,5,6-tetrafluorobenzotrichloride were placed in a 0.5 l four necked flask. After addition of 5.4 g of iron(III) chloride, the mixture was heated to 60° C. with stirring. 46 g of formic acid were metered in over 6 hours at 60°–65° C. Vigorous gas development (carbon monoxide, hydrogen chloride) began immediately. The gas stream was fed to an absorption tower via a cooler. After addition was complete, the mixture was further stirred for two more hours at 60° C. The product was then distilled under reduced pressure.

12.9 g of first runnings (GC analysis: 99.1%) and 163.5 g of main fraction (b.p.: 54°–56° C./20 mbar; GC analysis: 99.2%) were obtained. The overall yield was 83% of theory.

Example 2

4-Fluorobenzoyl chloride 300 g of 4-fluorobenzotrichloride and 1.5 g of iron chloride were placed in an apparatus comprising a 1 l four necked flask equipped with stirrer, thermometer, reflux condenser and dropping funnel. The mixture was heated to 80° C.

A total of 50 ml of formic acid were then metered in over 5 hours in such a manner that the temperature could readily be maintained. After this, 220 g of a mixture having the following composition were present:

89.8% 4-fluorobenzoyl chloride 1.5% 4-fluorobenzotrichloride 2.1% 4-fluorobenzoic anhydride 6.6% unknowns 185 g of 4-fluorobenzoyl chloride having a content of 99.1% (83% of theory) were obtained by fractional distillation. The distillation residue predominantly contained 4-fluorobenzotrichloride and can be recycled to the next batch.

Example 3

3-Fluorobenzoyl chloride 300 g of 3-fluorobenzotrichloride and 1.5 g of iron chloride are placed in an apparatus comprising a 1 l four necked flask equipped with stirrer, thermometer, reflux condenser and dropping funnel. The mixture was heated to 80° C. A total of 53 ml of formic acid were then added over 5 hours in such a manner that the temperature could readily be maintained.

After this, 217 g of a mixture having the following composition were present:

92.4% 3-fluorobenzoyl chloride 2.3% 3-fluorobenzotrichloride 1.7% 3-fluorobenzoic anhydride 3.6% unknowns From this, after fractional distillation, 190 g of 3-fluorobenzoyl chloride having a content of 99.3% (85% of theory) were obtained. The distillation residue predominantly contained 3-fluorobenzotrichloride and can be recycled to the next batch.

Example 4

2,3,4,5-Tetrafluorobenzoyl chloride a) 268 g of 2,3,4,5-tetrafluorobenzotrichloride were placed in a stirred apparatus and 5.3 [lacuna] of iron (III) chloride were added, 45 g of formic acid (98–100%) were pumped in over 8 hours at 60° C. Vigorous gas development (carbon monoxide, hydrogen chloride) began immediately. The gas stream was fed to an absorption tower via a cooler. After addition was complete, the mixture was stirred until the end of gas development. The product was then distilled. 195 g of 2,3,4,5-tetrafluorobenzoyl chloride were obtained (91.5% of theory); b.p.: 70°–72° C./20 mbar, $n^{D25}$: 1.4773.

b) 268 g of 2,3,4,5-tetrafluorobenzotrichloride were added to the distillation residue (approximately 20 g) and 2.7 g of iron(III) chloride were added. The mixture was reacted with formic acid in a similar manner to a). 198 g (93% of theory) of 2,3,4,5-tetrafluorobenzoyl chloride were obtained.

We claim:

1. Process for the preparation of ring-halogenated benzoyl chlorides, characterized in that ring-halogenated benzotrichlorides are reacted with formic acid in the presence of iron salts.

2. Process according to claim 1, characterized in that the ring-halogenated benzotrichlorides used are those of the formula (I)

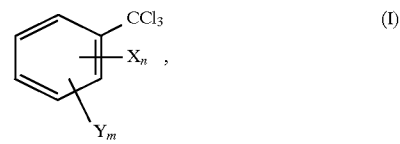

in which

X represents fluorine and Y represents hydrogen or chlorine and n denotes an integer from 1 to 5 and m=5−n.

3. Process according to claim 1, characterized in that 0.8 to 1.1 mol of formic acid is used per mole of ring-halogenated benzotrichloride.

4. Process according to claim 1, characterized in that the iron salt used is iron(III) chloride.

5. Process according to claim 1, characterized in that iron salts are used in an amount of 0.05 to 3% by weight, based on ring-halogenated benzotrichloride.

6. Process according to claim 1, characterized in that it is carried out at temperatures in the range 20° to 100° C.

7. Process according to claim 1, characterized in that the hydrogen chloride escaping during the reaction is absorbed in water and the carbon monoxide escaping during the reaction is burnt.

8. Process according to claim 1, characterized in that the ring-halogenated benzoyl chloride prepared is separated off by distillation from the reaction mixture present after the reaction.

9. Process according to claim 1, characterized in that the ring-halogenated benzoyl chloride prepared is separated off by distillation from the reaction mixture present after the reaction and the mixture containing iron salts remaining is reused in a further batch instead of fresh iron salts.

* * * * *

UNITED STATES PATENT AND TRADEMARK OFFICE
CERTIFICATE OF CORRECTION

PATENT NO. : 5,840,975                                  Page 1 of 2
DATED      : November 24, 1998
INVENTOR(S): Gehring, et al.

It is certified that error appears in the above-identified patent and that said Letters Patent is hereby corrected as shown below:

Col. 4, line 7       Delete " characterized in that " and
                     substitute -- wherein --

Col. 4, line 10      Delete " characterized in that " and
                     substitute -- wherein --

Col. 4, line 25      Delete " characterized in that " and
                     substitute -- wherein --

Col. 4, line 28      Delete " characterized in that " and
                     substitute -- wherein --

Col. 4, line 30      Delete " characterized in that " and
                     substitute -- wherein --

Col. 4, line 33      Delete " characterized in that " and
                     substitute -- wherein --

Col. 4, claim 7      Delete " characterized in that " and
line 1               substitute -- wherein --

UNITED STATES PATENT AND TRADEMARK OFFICE
CERTIFICATE OF CORRECTION

PATENT NO.   : 5,840,975
DATED        : November 24, 1998
INVENTOR(S)  : Gehring, et al.

It is certified that error appears in the above-identified patent and that said Letters Patent is hereby corrected as shown below:

Col. 4, line 40   Delete " characterized in that " and substitute -- wherein --

Col. 4, line 44   Delete " characterized in that " and substitute -- wherein --

Signed and Sealed this

Seventeenth Day of August, 1999

Attest:

Q. TODD DICKINSON

Attesting Officer         Acting Commissioner of Patents and Trademarks